(12) United States Patent
Wiseman et al.

(10) Patent No.: US 8,324,570 B2
(45) Date of Patent: Dec. 4, 2012

(54) METHOD AND SYSTEM FOR SURFACE SAMPLING

(75) Inventors: Justin Wiseman, Zionsville, IN (US); Nathalie Agar, Newton, MA (US)

(73) Assignees: Prosolia, Inc., Indianapolis, IN (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/249,716

(22) Filed: Sep. 30, 2011

(65) Prior Publication Data

US 2012/0080592 A1   Apr. 5, 2012

Related U.S. Application Data

(63) Continuation of application No. PCT/US2010/029586, filed on Apr. 1, 2010.

(60) Provisional application No. 61/165,635, filed on Apr. 1, 2009.

(51) Int. Cl.
*H01J 49/04* (2006.01)

(52) U.S. Cl. ........................................ 250/288

(58) Field of Classification Search .................. 250/288, 250/281, 282
See application file for complete search history.

(56) References Cited

U.S. PATENT DOCUMENTS

| | | | |
|---|---|---|---|
| 3,693,613 A | 9/1972 | Kelman | |
| 3,902,371 A * | 9/1975 | Hooper et al. | ............ 73/864.24 |
| 4,223,676 A | 9/1980 | Wuchinich et al. | |
| 4,827,911 A | 5/1989 | Broadwin et al. | |
| 5,306,412 A | 4/1994 | Whitehouse et al. | |
| 6,803,566 B2 | 10/2004 | Van Berkel et al. | |
| 8,203,117 B2 * | 6/2012 | Wiseman et al. | ............ 250/288 |
| 2004/0203175 A1 | 10/2004 | Li et al. | |
| 2005/0230635 A1 | 10/2005 | Takats et al. | |
| 2008/0156985 A1 | 7/2008 | Venter et al. | |
| 2008/0272294 A1 | 11/2008 | Kovtoun | |
| 2010/0317118 A1 * | 12/2010 | Masujima et al. | ............ 436/63 |

OTHER PUBLICATIONS

Cody et al. "Versatile new ion source for the analysis of materials in open air under ambient conditions," Anal Chem 2005, vol. 77, pp. 2297-2302.

Takats et al, "Mass spectrometry sampling under ambient conditions with desorption electrospray ionization," Science, 2004, vol. 306, pp. 471-473.

* cited by examiner

*Primary Examiner* — Kiet T Nguyen
(74) *Attorney, Agent, or Firm* — Sanjeev K. Mahanta; Michael I. Falkoff; Sonia K. Guterman

(57) ABSTRACT

A system and sampling probe adaptable to an ultrasonic surgical instrument applies irrigation fluid and ultrasonic or vibrational energy to a target, and aspirates material desorbed from the target into a pick-up conduit. A suction source at the distal end of the conduit may aspirate the material released from the target with the irrigation fluid, thus efficiently sampling a broad range of materials from an arbitrary target to produce an analyzable effluent analyte stream which may be ionized and provided to the inlet of an ion-type analysis instrument, or may be fed directly to an instrument such as a flow cytometer, IR or fluorescence spectrophotometer, or other analyzer. Carrier gas may be provided to more effectively transport the desorbed material, and the probe may be incorporated into a robotic device to automatically carry out surface imaging or to effect sampling in hazardous environments.

30 Claims, 11 Drawing Sheets

METHOD AND SYSTEM FOR SURFACE SAMPLING

RELATED APPLICATIONS

The present application claims the benefit of U.S. provisional application Ser. No. 61/165,635 filed in the U.S. Patent and Trademark Office Apr. 1, 2009, and is a continuation of and claims the benefit of international application PCT/US10/29586 filed Apr. 1, 2010 and published Oct. 7, 2010, each of which is hereby incorporated by reference herein in its entirety.

FIELD OF INVENTION

The present invention relates to sampling and detection of material such as atoms, molecules, molecular clusters and intact cells or other material present on and removed from a target object for analysis. The method employs a probe which applies vibrational or ultrasonic energy to the target object to desorb or release analytes from the target, and aspirates the desorbed material forming an analyte effluent for presentation to an analysis instrument, such as a mass spectrometer, flow cytometer, spectrophotometer or other analysis instrument.

BACKGROUND OF INVENTION

Surface analysis by mass spectrometry (MS) has traditionally been performed with a sample positioned in the vacuum environment of an analysis instrument, applying desorption/ionization (DI) techniques such as secondary ion mass spectrometry (SIMS) or matrix-assisted laser desorption ionization (MALDI). Other notable techniques include fast atom bombardment (FAB) and plasma desorption (PD). In addition to MALDI performed under high vacuum conditions, an atmospheric pressure version of the MALDI method has been developed and is also commercially available. Methods for DI under vacuum are numerous and generally fall into one of two categories, employing either particle or photon bombardment. While SIMS uses energetic molecular or atomic clusters to eject and ionize analyte from a conductive surface, MALDI creates ions of the analyte in a sample under vacuum conditions using laser pulses. The high vacuum environment of these processes poses inherent limitations to the type of sample and to the physical size and shape of sample that can be analyzed. These limitations often make it necessary to perform several sample preparation steps prior to analysis, thus also limiting the throughput of the method.

Ambient DI methods were developed to overcome the limitations of the high vacuum DI methods and to permit the direct analysis of ordinary objects outside the vacuum chamber, in the open atmosphere of the laboratory or while the sample is in its native environment. The preeminent method in this new field is Desorption Electrospray Ionization (DESI). Instrumentation for performing DESI procedures has been commercialized by Prosolia, Inc. (Indianapolis, Ind. USA). These specially designed sampling/ionization sources can be applied directly to an object at hand, operating to remove molecules from the surface and carry ions in a stream of small volume that can be directed to a mass spectrometer for analysis. Thus DESI produces an analyzable sample that requires no pretreatment. DESI systems permit analyte molecules to be removed from their initial object environment with spatial resolution, and preserve critical chemical information without the dilution or physicochemical modifications or breakdown that characterize the conventional sample extraction or conditioning devices or protocols which rely upon chemically harsh or physically energetic operations. In most instances, these DESI ion sources operate in ambient atmosphere, opening the way for mass spectrometry to be used routinely within a clinical, medical, industrial or other field environment.

Numerous methods for analyte DI have been demonstrated since the first report of DESI in: Takats, Z., Wiseman, J M., Gologan, B. & Cooks, R. G., Mass spectrometry sampling under ambient conditions with desorption electrospray ionization, *Science* 306, 471-473 (2004); and since the first report of Direct Analysis in Real Time (DART) in: Cody, R. B., Laramee, J. A. & Durst, H. D., Versatile new ion source for the analysis of materials in open air under ambient conditions, *Analytical Chemistry* 77, 2297-2302 (2005). However, despite these recent advances in surface sampling mass spectrometry, significant challenges still remain with respect to desorption and ionization of analytes from surfaces since the analyte and the substrate may each present a wide range of different characteristics and chemical matrices.

Ideally, an ambient DI method would be minimally destructive to the sample and would limit fragmentation or break-down of the analytes. While the latter is advantageous, the former poses limitations since solvents or energetic processes are generally used to promote desorption. This capability is, however, important if direct analysis methods are to find success in uncontrolled environmental conditions that occur in field use, where irregular surface shapes having different physical and chemical properties are to be expected. Therefore, the development of new methods having the capacity to efficiently disrupt the interaction of analytes bound to or within a target surface, and to extract desired analytes for analysis in an instrument non-proximate to the device, is a highly desirable capability that is inadequately achieved by the current methods.

Another limitation of current methodologies is the requirement for precise alignment of the desorption/ionization source with the target object and with the sample-receiving inlet of the analysis instrument. An improvement to circumvent issues with misalignment was described in published United States Patent application 2008/0156985 of inventors Venter and Cooks. That published application describes a fixed geometry approach having a sprayer, a MS inlet and a sample surface brought together in a small pressure-tight enclosure. That configuration can extract desorbed material into a small volume of carrier gas that may be effectively input to a vacuum-type analysis instrument without degrading the instrument measurement capabilities. The enclosure also serves to protect the user from harmful aerosols that may be produced under particular experimental conditions. While that methodology constituted an advance, it remained restricted in its ability to be oriented properly to a target surface, since the spray and inlet are fixed within an enclosure.

U.S. Pat. No. 6,803,566 discloses a method for analyzing surface micro-arrays of analytes using an electro spray-based system. The method utilizes a probe for delivering an eluting solvent which is made to flow across a spot, for example of component disposed in a gel separation bed, eluting the target component. The solvent is in contact with the sample and forms a stable liquid junction. The prerequisite for forming a stable liquid junction between the solvent and the sample surface poses limitations on analysis. For example, the sample surface must be substantially flat and have appropriate physico-chemical properties to allow formation of the liquid junction.

Ultrasonic devices are those which operate in frequency ranges between approximately 20 kHz-10 MHz. Some devices, operating in the audible range from 10-20 KHz are also classified as ultrasonic devices. Devices that utilize ultrasonic energy are used frequently for a variety of applications and are readily recognized in various arts where the effects are used for purposes such as cleaning objects, breaking down material or emulsifying liquids. One common use of ultrasonic energy is in prophylactic dental equipment for professional tooth cleaning. Ultrasonics are also used ophthalmically for emulsification and removal of cataracts in the eye, and surgically for endoscopic destruction and removal of gall- or kidney stones. Additionally, ultrasonic surgical tools have seen increasing use for specialized fragmentation and removal of soft tissues, such as for tumor resection in the brain or uterus. Ultrasonic surgical devices operate by inducing cavitation in the biological fluid of a tissue, fragmenting the tissue into small components that can be removed from the body of the patient. These devices commonly incorporate a provision for irrigating the surgical site and a port for suctional removal of the fluid and tissue fragments from the treatment site. The material so removed is directed to waste or preserved for histological examination. See, for example, U.S. Pat. No. 4,827,911.

SUMMARY

A novel method for desorption and sampling of analytes from a surface utilizes vibrational or ultrasonic energy (hereafter referred to as simply "ultrasonic" energy for brevity). The method, and a corresponding ultrasonic surface sampling probe ("USSP" or simply "probe"), operates at or near atmospheric conditions and expeditiously releases and samples material from the target surface into the probe. The probe may couple to diverse analysis instruments. The probe incorporates a first, vibrating metal capillary or contact member mounted within a hand piece, and a transducer that couples ultrasonic energy to the hollow capillary or other contact member, thus applying the vibrational energy to the surface which is to be probed. For example, the capillary may be constructed of, or mounted to, a stiff metal shaft that conducts the energy to an end thereof and couples the energy to the surface by contact with the surface. The capillary or shaft may have low acoustic impedance, being formed of titanium or a titanium alloy, or the transducer may be configured to launch a specific low-sound speed waveform into the capillary (such as a shear wave propagated in the thin capillary wall) so as to enhance the coupling of energy into a probed sample of different acoustic impedance, or the capillary or shaft may be actuated with standard compressional waves or vibratory motion to impart ultrasonic energy to the probed surface. An irrigation conduit which may, for example, be a second capillary positioned co-axial to the first capillary, or may be another conduit or port opening near the mouth of the first capillary, delivers an irrigating fluid to the site of analysis on the surface. In some embodiments, ultrasonic energy may be coupled to the surface via the irrigation fluid instead of, or in addition to, being coupled by direct contact between the probe tip. The positions and functions of the first and second capillaries may be interchanged, one functioning to irrigate and the other functioning to pick up fluid with material ultrasonically released from the surface.

In operation, the ultrasonic energy applied by the probe to the irrigated surface causes or enhances desorption of analyte material from the target object, into the fluid. An aspiration system may be provided to draw the analyte material into the capillary from the probed site on the surface. The aspirating system for removing fluid and surface material from the site of analysis may be implemented by a suction connection to the probe hand-piece or, more generally, connected at the end of the pick-up capillary distal to the sample surface.

When the analyte is to be passed to an ion-type mass analysis device, that is, a device that operates upon ions of sampled material, such as an ion mobility analyzer, an ion mass spectrometer or other such instrument, a transfer tube may connect to the aspirating system and direct the sampled analyte as a stream to an ionizer assembly that ionizes analytes in the desorbed sample which have been removed by the probe from the target surface via the capillary. In this case, the ionizing assembly may be the existing inlet stage of a mass spectrometer, or may be incorporated as a separate assembly between the aspirating system and the analysis instrument. For other types of analysis, the analyte sample or effluent stream may pass without being ionized to an instrument such as a UV or IR detector, or to a spectrometer to detect absorbance or emission spectra, or detect special markers. The probe is also effective for passing non-ionized sample material to other types of detection instrumentation, such as to a flow cytometer, to count, characterize, analyze or detect specific properties of particles or other material removed from the surface.

Analyte desorption from the surface is accomplished via dissolution or release of the sample by the irrigating fluid acting in concert with the applied ultrasonic energy. As such, the ultrasonic energy enhances and accelerates desorption, and extends both the depth of sample interrogation, and the range of analytes that will be desorbed into the irrigation fluid, by one or more physical mechanisms that effectively disrupt the binding or structure holding the analyte in or at material of the probed surface. Mechanisms causing the surface to release analyte—adsorbed atoms or molecules, whole cells, or intracellular or endocellular components and other material—may include local shock—induced stress, cavitation or the like, or may include mechanical mechanisms such as vibratory shear imposed by the vibrating fluid-to-matrix contact at the site of analysis, as well physico-chemical effects lowering or disrupting barriers such as surface energy, relative dilution, energy of solvation, or the enhancement of diffusive or rheological migration of analyte, including adhered, bound or poorly-mobile analyte from the target matrix material into the fluid.

The desorbed matter is swept or aspirated into the transfer or pick-up capillary and the analyte is carried with the aspirated fluid. While large particles may be removed from the surface as "chunks", configurations of the instrument may largely suppress such unsuitable material in the analysis stream because such chunks may exhibit sufficient momentum that they are not swept into the sampling capillary, thus not reaching the ionization assembly if one is present; or such material may be separated after passing through the capillary following a downstream ionization stage by their different trajectories ahead of the mass spectrometer or other analysis instrument. However the configuration of the probe and the pick-up capillary, together with the effects of higher frequency vibrational excitation, provides predominantly smaller particles, cells, molecules, atoms desorbed into the irrigation fluid, and swept by the dynamic drag of the aspirating system into the pickup capillary and along the described analysis path.

The probe of the invention and analysis systems including the probe as a sampling instrument extend the range and convenience of conventional instrumentation. Systems employing the ultrasonic probe may be operated to analyze pharmaceutical compounds and metabolites in urine, blood, fecal matter, and tissue; and may be applied to the analysis of surfaces such as vinyl flooring or stainless steel, substrates such as fabric or animal tissue, and other samples for the detection and determination of forensic, pharmaceutical or other residues. The method is applied to the analysis of surfaces such as concrete, timber and asphalt, for example to detect signature residues of chemical weapons or explosives; or is applied to the analysis of foods for the detection and identification of pesticides, adulterants, toxins or chemicals; or is applied to the in vivo analysis of tissue for the determination of tumor margins or detection of particular markers of disease or for any type of surgical application to optimize the definition of surgical boundaries, or for the detection and quantification of drug uptake.

BRIEF DESCRIPTION OF DRAWINGS

These and other features of the invention will be understood from the description herein and the claims appended hereto, taken together with the Figures showing exemplary embodiments and variations, wherein:

DETAILED DESCRIPTION

Figure 1:
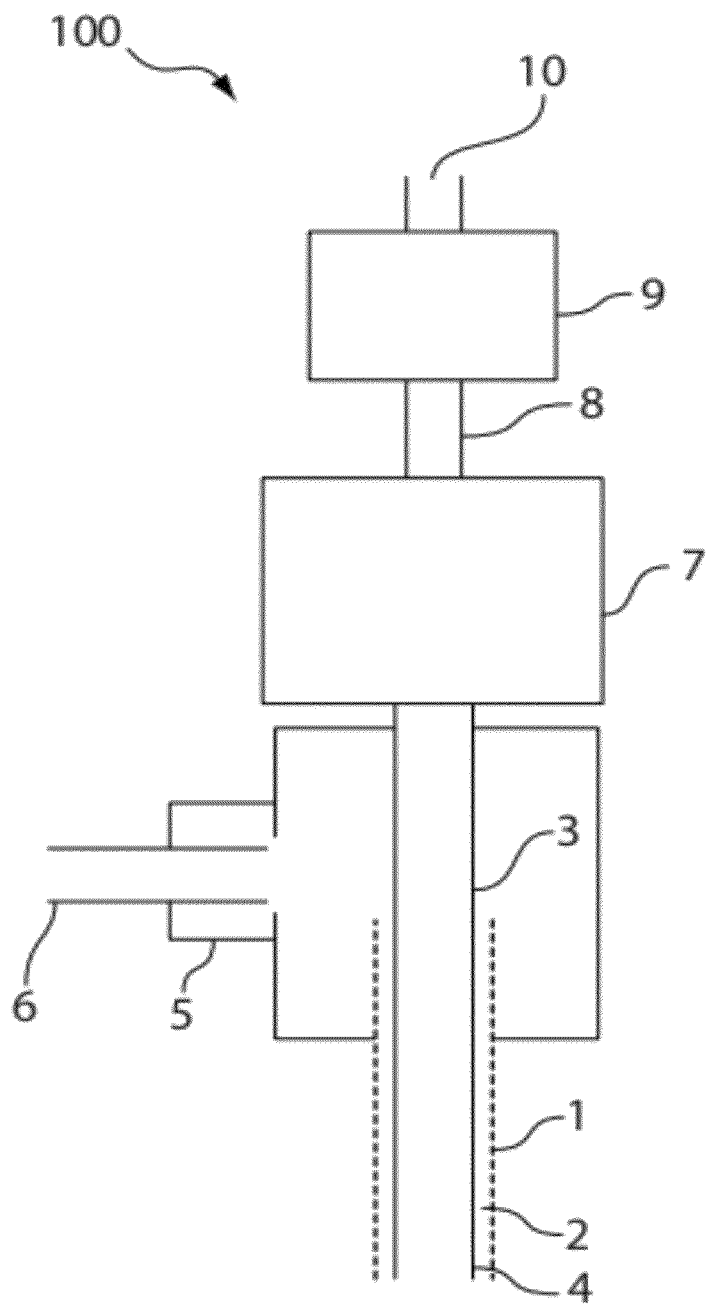
FIG. 1 shows a schematic drawing of the ultrasonic surface sampling probe of the present invention.

The present invention is a probe system intended to function at or near atmospheric pressure and in uncontrolled conditions as well as in more controlled environments, such as those found in a laboratory, a clinical setting, an operating theatre, a manufacturing facility or a screening center. One or more objects are to provide a device and method that delivers energy to a target surface to disrupt analytes bound to or within the target, and effectively desorb and remove a sample of such analytes from a wide variety of surfaces having different physical and chemical properties, preferably without requiring for pre-treatment or specialized preparation of the sample. The surface sampling method may employ a probe adapted to the method steps to rapidly and repeatably pick up directly analyzable samples of analyte from a target surface. The probe may be substantially hand-held to enable the user to select sites for sampling on ordinary objects in the open atmosphere, or may be a machine-manipulable probe adapted for automated surface sampling. In one embodiment the probe applies sufficient energy to disrupt live tissue for the analysis of cellular contents and/or extracellular matrix material in vitro or in vivo, for example, to detect specific material or to determine tumor margins in real time.

Analytes sampled by the present invention are presented in an aspirated stream for analysis by a mass spectrometer or other instrumentation capable of analyzing atoms, molecules, molecular clusters or intact cells. The mass spectrometer may be a time-of-flight, ion trap, quadrupole, triple quadrupole tandem mass spectrometer or other instrument. In one aspect the invention is a method for desorbing and ionizing an analyte in a sample comprising contacting the sample with a vibrating probe. The probe may utilize a vibrating, hollow metal capillary for contacting the sample, and includes a conduit for irrigating the site of analysis with a solvent, carrier or other fluid. The irrigation solvent may be selected based on the target analyte(s) and/or known surface properties to optimize the release and pick-up of analyte. For example, a substantially alcohol- or water-based irrigation solvent may be chosen when it is desired to sample and identify analytes that are soluble in alcohol or water. The combination of ultrasonic vibration and provision of irrigation fluid serves to dissolve or otherwise promote release or desorption of analytes from the sample matrix or surface, and their partition into the irrigant, and also contributes to the dependable and repeatable aspiration of the sampled material into the capillary assembly and its transport to the mass spectrometer or other instrument for analysis. The irrigation fluid may also be a mixture compounded to selectively pick up or carry certain target analytes over other materials that may be present in the substrate, and may include reactive components to cleave, protonate or otherwise condition the released material. When relatively high levels of ultrasonic energy are applied, the irrigation fluid assembly may also be configured or operated to dissipate heat generated by the vibrating metal capillary, i.e., to act as a cooling fluid, for example to maintain relatively stable thermal conditions at the sampling site. In some embodiments a second cooling fluid may be introduced to limit or dissipate vibrationally-generated heat at the probe tip, and all or a portion of the second fluid may be directed to waste prior to reaching the analytic instrumentation.

Thus the present invention combines the effects of ultrasonic energy to drive dissolution, release or desorption of material from the surface of a target which is to be probed, and aspirates the material to provide an analyte sample. The combination of these mechanisms allows a wide variety of surfaces to be interrogated without specialized sample preparation or extraction, and operates effectively for a wide range of analyte/surface combinations of greatly different physical and/or chemical properties to remove analyte from the surface while introducing only a small amount of irrigant or carrier fluid to the sample stream.

In one embodiment, the ultrasonic driver frequency is about 40 kHz, and the capillary passage is held in a tip assembly that is driven such that the tip has a relatively small net displacement, of a few thousandths of an inch or less. However higher or lower frequencies, and greater or smaller signal amplitudes or displacements may be applied, and the invention further contemplates many variations in construction. Thus, the tip assembly may include a softer, compliant contact at its end, or may include a hybrid shape, that optimizes coupling of vibrational energy into the target surface material or irrigated surface, or may include two surface-contacting members or capillaries driven in opposite phase to more effectively deliver energy to the local site and release analyte therefrom. Further, various forms of ultrasonic driver may be used, such as a piezoelectric crystal, a magnetorestrictive metal rod, a piezocomposite material, or other ultrasonic actuator known in the art. Since it is not feasible to predetermine the optimal instrument settings for all object/analyte pairs that may be encountered, the probe system in one embodiment preferably includes an adjustable control to vary a parameter such as vibrational energy, and/or frequency of vibration to allow the user to determine or adapt the operating characteristics and optimize them to a specific target surface or to release of a specific analyte of interest in a range of materials which the user may encounter. Thus, driving frequencies as low as a few hundred Hz may be used for desorption of relatively simple and soluble components, while frequencies of 20-80 kHz or higher may be required for effectively enhancing desorption of a spectrum of analytes, including, for example, analytes of high molecular weight, or for lysing biological tissue structures and/or desorbing large molecules or bound material and related biological material.

The application of ultrasonic energy is believed to enhance the desorption or release of analyte by several physical mechanisms, which may include transport or separation mechanisms additional to solvation, for example promoting migration of viscous material, desorption of adhered analyte, emulsification of immiscible hydrophilic/hydrophobic analyte/fluid systems, disruption of membrane or pore structures, vibrational nebulization and numerous other effects such that unknown or arbitrary analytes are released from the target surface, enter the irrigation fluid, and are aspirated to form a sample stream for detection or analysis in solution, emulsion, as a nebulized material or microemulsified aerosol, or otherwise, without resort to special lab-specified solvent, separation or conditioning protocols. However, performance improvements may also be obtained for particular analytes by formulating the irrigation fluid to enhance desorption of the particular analyte, to inhibit breakdown of its chemical structure, or otherwise condition the material in the aspirated stream for ionization, transport or downstream analysis.

One example of a probe for field operations to screen for the detection of chemical weapons or residues is a surface sampling device that is hand-held, easily manipulated and substantially light weight, so the user's other hand is free to manipulate the object of interest for analysis. The present invention fulfills this need and more. The hand-held probe may be readily integrated with a dedicated sensor, for example, in which the aspirated sample is fed directly into a solid state or other co-mounted detector that has been constructed to respond to traces of a specific explosive, drug, chemical agent or biological agent.

In another aspect of the invention the analyte sampling method of the invention is used in tandem with an ionization stage to create ions of the analytes picked up by the probe mechanism, and the ionized sample is then analyzed by an in-line general analysis instrument. The ionization method could be any atmospheric ionization method including electrospray ionization (ESI), sonic spray ionization (SSI), atmospheric pressure chemical ionization (APCI), DART, or the flowing afterglow of an atmospheric pressure glow discharge. The ionization method may also be a laser based system in which the analyte of interest is ionized by laser pulses.

In another aspect of the invention the method incorporates a means for providing a flow of carrier gas (e.g nitrogen, an inert gas, air or mixtures thereof) to aid in transporting the desorbed analyte from the probe to downstream analysis instrumentation, for example into the transfer tube for ionization and subsequent analysis by a mass spectrometer or other chemical detection system. The carrier gas may be applied to blanket the analysis site, and may be selected for compatibility with the analysis instrument (such as an ionizable noble gas) and/or compatibility with chemistry of the target analyte. In a probe embodiment having several coaxially-positioned capillaries for providing irrigation, carrier gas flow, contact vibration and sample pick-up, the carrier gas may be fed through an outer capillary with respect to the irrigation capillary, and both may be directed towards the site of analysis. Coaxial tube arrangements for carrier, irrigant and sample pick-up allow the probe to provide precise or point-wise spatial control of the sampling site. Alternatively, irrigation and pick-up capillaries may be spaced apart and directed across axes to intersect at the sampled site, as shown in FIG. 1A.

In another embodiment of the invention, the method incorporates two vibrating hollow metal capillaries positioned co-axial to one another and operating 180 degrees out of phase with each other but at a common frequency to enhance efficiency of surface energization and analyte desorption. In another aspect of the invention, the amplitude of oscillation is manipulated to adjust the energy of desorption of analytes. For a number of analytes and physical structures, the frequency of longitudinal oscillation may be set to a frequency and/or amplitude that is optimized for sampling of the analyte, or adapted to the surface's physical structure and/or chemical characteristics.

In other aspects of the invention, the probe may include two vibrating hollow metal capillaries positioned co-axial to one another and operated at different frequencies, and or may include an adjustable controller to also set the amplitude of vibration so as to preferentially apply more or less stress to the sample surface.

In another aspect of the invention, the device may be, or may be incorporated in, a tool for removing undesired regions of a surface, such as a tumor region on skin or other tissue, and subjecting those regions to chemical analysis. In this aspect the probe applies an ablating or otherwise destructive level of energy to the surface or tissue and the ablated material may be picked up with the fluid and gas via the capillary or via a secondary suction assembly positioned near the probe tip.

In another aspect of the invention, the probe is mounted on a robotic platform and is automatically positioned with respect to the sample surface having motion in three dimensions, X, Y, Z, and rotation between the XY, XZ, or YZ axis. Alternatively the probe may be stationary and positioned orthogonal to the plane of a robotic platform having motion in three dimensions, X, Y, and Z on which the sample is placed for analysis.

Figure 1A:
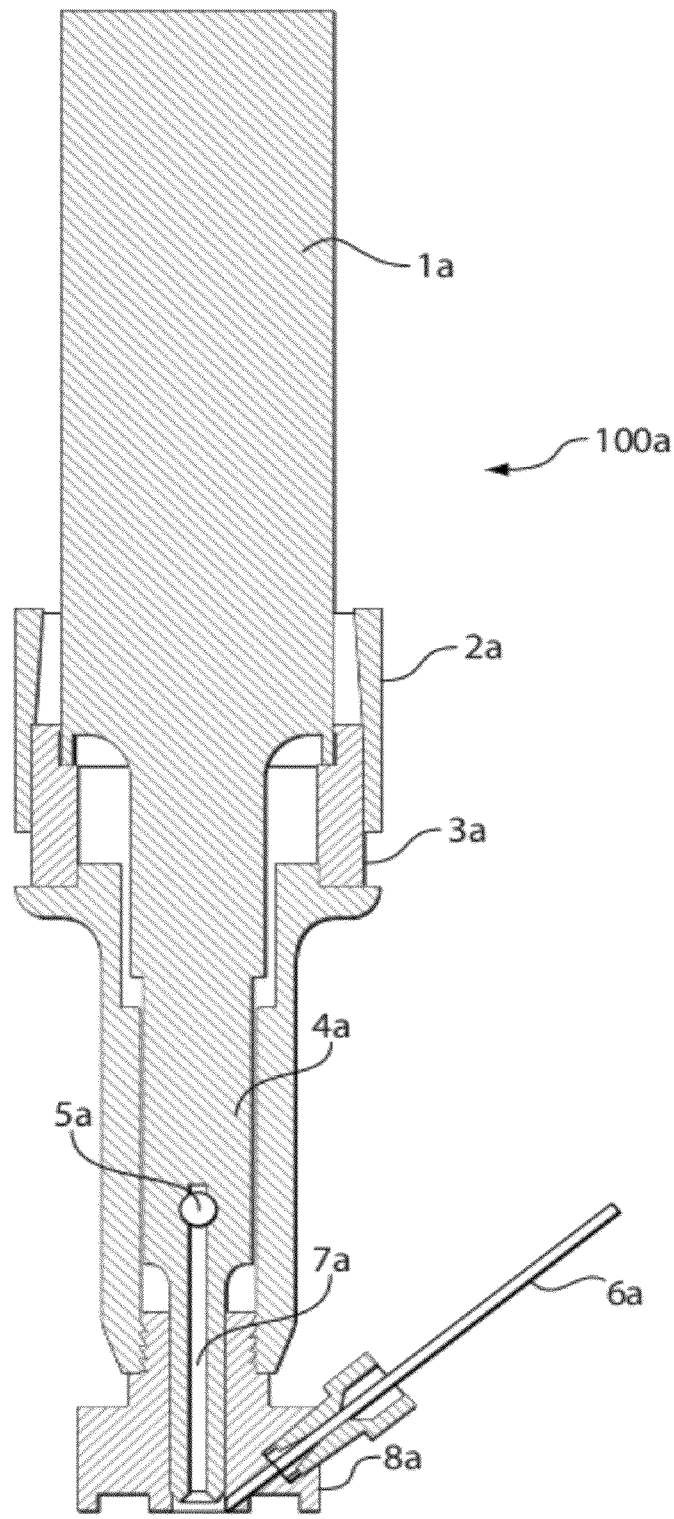
FIG. 1A shows an engineering drawing of another embodiment.

Turning now to FIG. 1, there is shown in cross section a probe 100, having a sonication member 3 for applying vibrational energy to the target surface. Member 3 includes a capillary comprising a metal such as titanium, stainless steel or tungsten, or a suitable composite or polymeric material, such as a piezoceramic in an epoxy matrix, or a piezoelectric plastic such as polyvinylidenefluoride (PVDF), preferably having low acoustic impedance. An irrigation conduit 1, which in this embodiment is also a capillary or small tube, has an outlet end positioned at the probe end, to provide irrigation fluid 2 which may be fed to the irrigation capillary 1 through the irrigation port 6 and the irrigation connector 5. The probe inlet end of the sonication probe 3 consists of a sampling tip 4 while the distal or probe outlet end of the sonication probe 3 is coupled to an ultrasonic transducer 7 which provides vibrational energy, for example in the ultrasonic frequency range of 40-80 kHz, in the sonication probe, 3. The transducer may alternatively be acoustically coupled closer to the sampling tip 4, and the probe 3 may be implemented as a short stub which applies vibrational energy to the surface and picks up desorbed analyte, with a tube connection at its upper end. When the probe 3 is contacted to a target sample, sonication and local shock-induced stress imposed by the vibrating probe 3 act to disrupt the surface, releasing analyte atoms, molecules or cells. Desorbed analytes enter the irrigation fluid 2 and the aspirator 9 produces dynamic draw to aspirate the desorbed analytes into the sampling tip 4 through the capillary and into the connecting body, 8, for delivery of the analyte/effluent 10 to an analysis instrument. Large particles which are removed from the surface as 'chunks' may exhibit sufficiently large momentum to avoid aspiration into or transport through the pick-up capillary of the sonication probe, whereas smaller analyte particles, atoms, molecules and cells are aspirated into the sonication probe, 3. In one embodiment of the invention, the temperature of the irrigation fluid 2 is adjusted to be at least cooler than room temperature and thus act as a cooling fluid to dissipate heat generated by the vibrating sonication probe, 3. In another embodiment, a drive signal for the transducer 7 is adjusted to control the amplitude of oscillation in the sonication probe 3 in order to change the energy applied for desorption of analytes or to add more or less stress to the sample surface. In a further embodiment, the transducer 7 can be adjusted to manipulate the longitudinal oscillation of the sonication probe 3 to an optimal frequency for the physical and chemical characteristics of a particular sample surface. Thus, disruption of the surface may be accomplished at energies that break cell walls, or at frequencies having a characteristic wavelength corresponding to a resonance of a target structure so as to preferentially disrupt the target structure or cause cavitation. Frequencies as low as several hundred Hz may be used when the target analytes are material of a type to be readily desorbed from the surface, or readily soluble in the irrigant, while higher acoustic and ultrasonic frequencies may be employed when more vigorous or resonant excitation is required to effect desorption or release.

FIG. 1A shows a CAD model of a prototype ultrasonic surface sampling probe 100a in cross section. An ultrasonic transducer assembly in a handle portion 1a attaches via a probe collar 3a and retaining ring 2a to couple ultrasonic energy to a probe tip 4a. Tip 4a is machined of titanium, and has a central bore containing or defining a first fluid inlet/outlet channel or capillary 7a with fluid end 5a. Tip 4a is secured against a vibrating seat or otherwise acoustically coupled to the transducer in the body 1a, and shaped to conduct the ultrasonic signal to a sampling tip and apply the energy to the surface being sampled. An adjustable probe head assembly 8a carries a second fluid inlet/outlet channel or capillary 6a. The illustrated probe head 8a is threaded to adjust vertically (i.e., along the axis of tip 4a), and carries the second inlet/outlet channel or capillary 6a at an angle opening near to the contact point of tip 4a and first inlet/outlet channel or capillary 7a. In this embodiment, the capillaries are interchangeable—that is, either one maybe used for irrigation, and the other for aspiration of desorbed material. In other embodiments, the head 8a may be configured to swivel to a different angle or non-axial alignment. The channels 6a, 7a may generally have an internal diameter ranging from quite small, say about 0.1 mm, to 5 or even 10 mm. One prototype had a 2.3 mm inner diameter.

In operation, the ultrasonic energy may disperse the desorbed material and irrigant into small droplets, and the droplet size is frequency-dependent. Higher frequencies produce smaller droplets. Generally, the initially-formed droplets will become smaller over time due to solvent evaporation; smaller semi-volatile and volatile molecules will evaporate off with the solvent. When such molecules are ions within the droplets, they can be detected when passed to a mass spectrometer. Certain materials can also become ionized in the gas phase through gas phase chemical reactions with ionized species present in the ambient air (such as $H_3O^+$). As solvent continues to evaporate off the droplets, excess charge in the droplets will be picked up by larger molecules, which are then detected when swept into the inlet of a mass spectrometer. The process can be made more efficient by coupling the output of the ultrasonic surface sampling probe to a second ionization source that creates excess charged species in the gas phase ahead of the entrance to the mass spectrometer. This can be done by glow discharge, UV laser, infrared laser electrospray or other mechanism.

Figure 2:
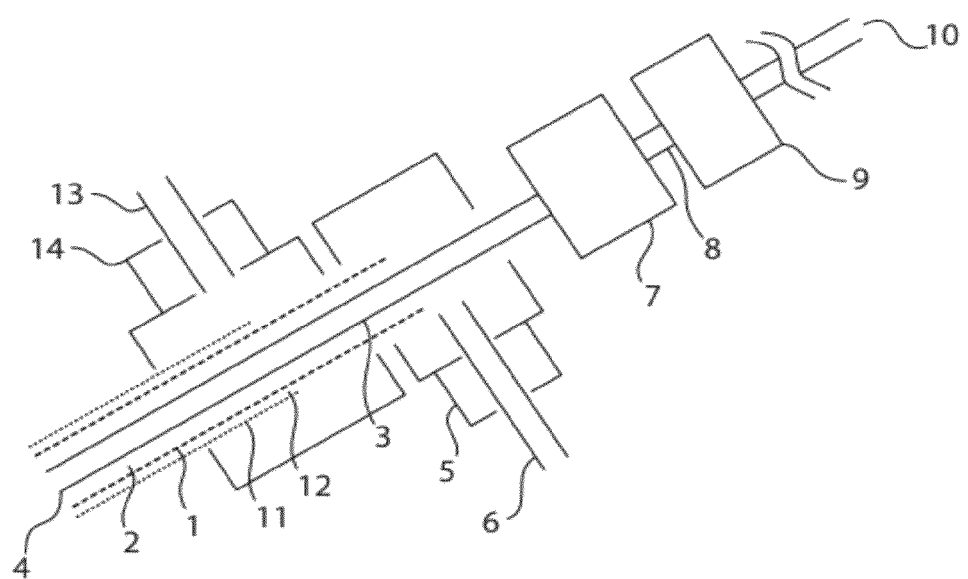
FIG. 2 shows an embodiment of the ultrasonic surface sampling probe having coaxially mounted capillaries for carrier gas and irrigation fluid.

FIG. 2 shows an embodiment of the system 100 having a carrier gas capillary 11 located coaxial to the sonication probe 3 and the irrigation capillary 1 for enhanced transport of the analyte stream. Carrier gas 12 enters the carrier gas capillary 11 through a carrier gas port 13 and carrier gas connector 14, providing a gas flow through the carrier gas capillary 11 to enhance transport of the analytes desorbed from the target into and through the probe pick-up. The carrier gas 12 is an inert or non-reactive gas such as nitrogen, argon, helium or air, which is provided at a rate effective to aid in transporting the desorbed analyte into the sampling tip 4, through the capillary 1 and into the output connector 8 for delivery of the analyte effluent stream 10.

Figure 3:
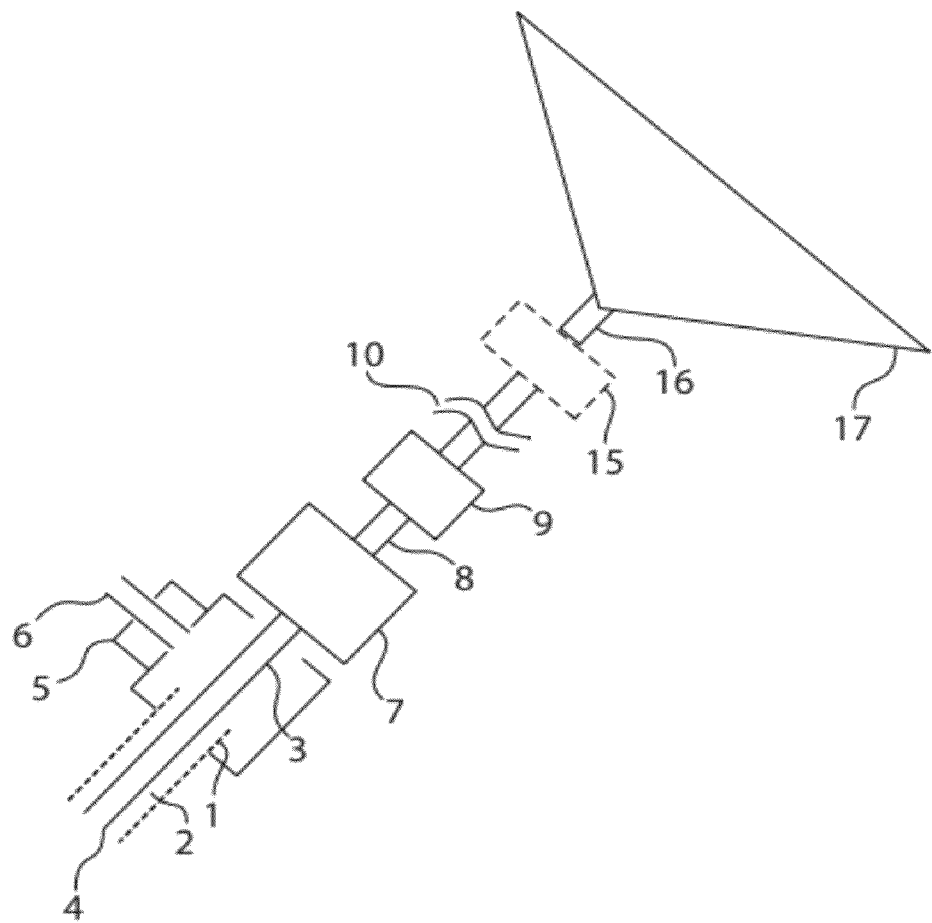
FIG. 3 depicts an embodiment of the probe having an ionization assembly between the probe sample effluent and the inlet of a mass spectrometer or analyzer.

FIG. 3 shows an embodiment of the system 100 incorporating, or having a location for attachment of, an ionization assembly 15 to ionize the effluent analyte at a position downstream of the pickup capillary. Assembly 15 may, for example, be an operative ionization assembly or ionization source such as is used for a process selected from a group including spray ionization such as electrospray (ESI), gas-phase ionization such as DART, laser-based ionization such as UV or IR based ionization, glow discharge ionization or other known ionization processes. Ionization source 15 is located between the aspirator 9 and the atmospheric inlet 17 of the instrument for analyzing sample molecules. The instrument may be any analysis instrument that receives ionized material as an input. Thus, for example, the analyzer may be an ion mass spectrometer, a quadrupole mass spectrometer, a triple quadrupole tandem mass spectrometer, an ion mobility analyzer or other ion analysis instrument. When the probe is configured without an ionization stage 15, the analyte effluent may be provided to an analysis instrument such as a UV or IR flow cell to detect specific fluorescence peaks, or to other fluorescence detection instrument, for example to monitor drug accumulation during tumor treatment; or the effluent stream may be provided to an instrument such as a flow cytometer to detect cells, cell types or marked particles. The analyte is aspirated into the sampling tip 4, through the capillary 1 and into the connecting body 8, for delivery of the analyte-containing effluent 10 into the ionization source 15, if present, and then to the analysis instrument, via the second connecting body 16.

Embodiments of probe 100 as described above greatly extend both the range of analytes and the effectiveness of sampling achievable for essentially unconstrained field targets, allowing a small volume of irrigation fluid to quickly and efficiently remove and transport analyte samples from a point-like or small region of a target surface. By applying vibrational energy at a frequency in the audio spectrum, enhanced desorption is obtained for many materials, while frequencies in the 10-100 kHz range or higher may introduce further effects of cavitation of the material structure, or nebulization of the desorbed material, for enhanced aspiration. The broad adaptability of the probe to different analysis instruments provides further flexibility. In some circumstances it will be desired to further build up or break down (or both) the effluent analyte stream from the probe. In other circumstances, the selected analysis instrument may possess its own additional sample-conditioning system in a front-end input stage that aspirates, dilutes, provides a carrier for, or de-solvates the effluent analyte sample stream from the probe.

Figure 4:
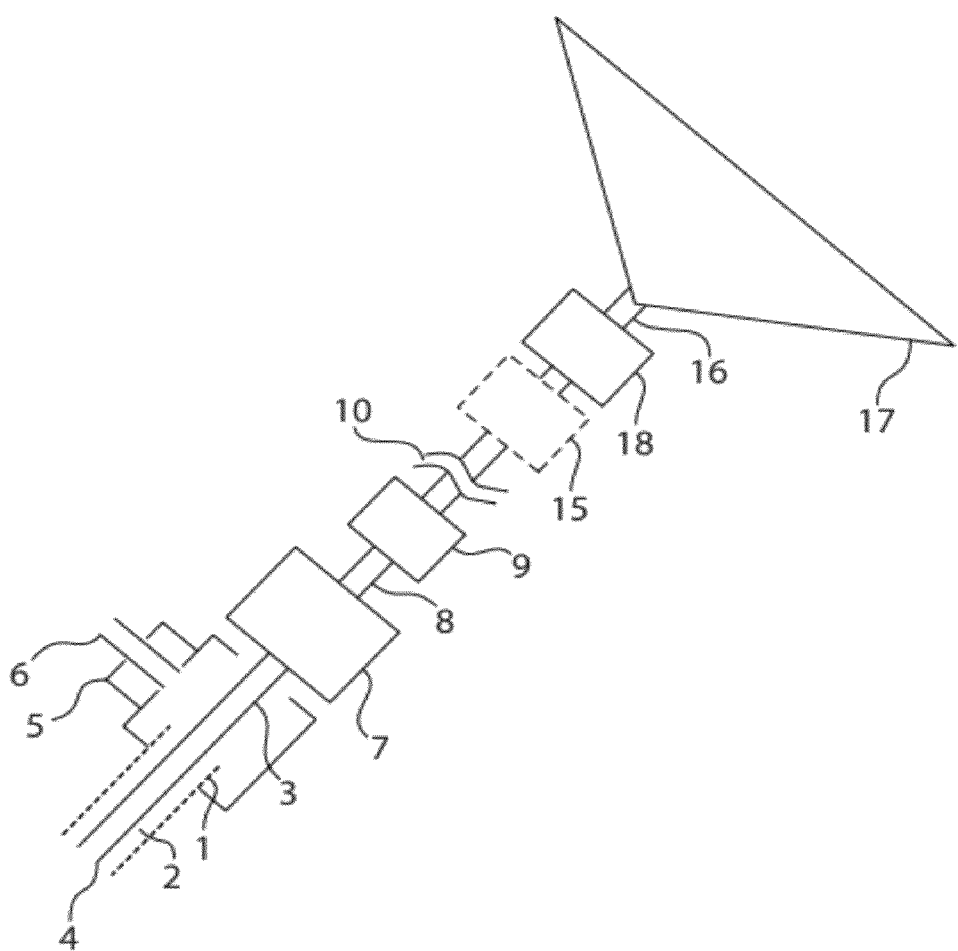
FIG. 4 depicts an embodiment of the probe including an ionization region 10 between the effluent from a first aspirating system and a second aspirating system of higher flow relative to the first aspirating system, which is connected to the inlet of a mass spectrometer.

FIG. 4 shows an embodiment of the system 100, having a second aspirator 18, located between the ionization assembly 15 and the analysis instrument 17. In this embodiment, the removed analyte is ionized, and analyte ions are aspirated from the ionization assembly 15, through the connecting body 16, and into the instrument 17.

Figure 5:
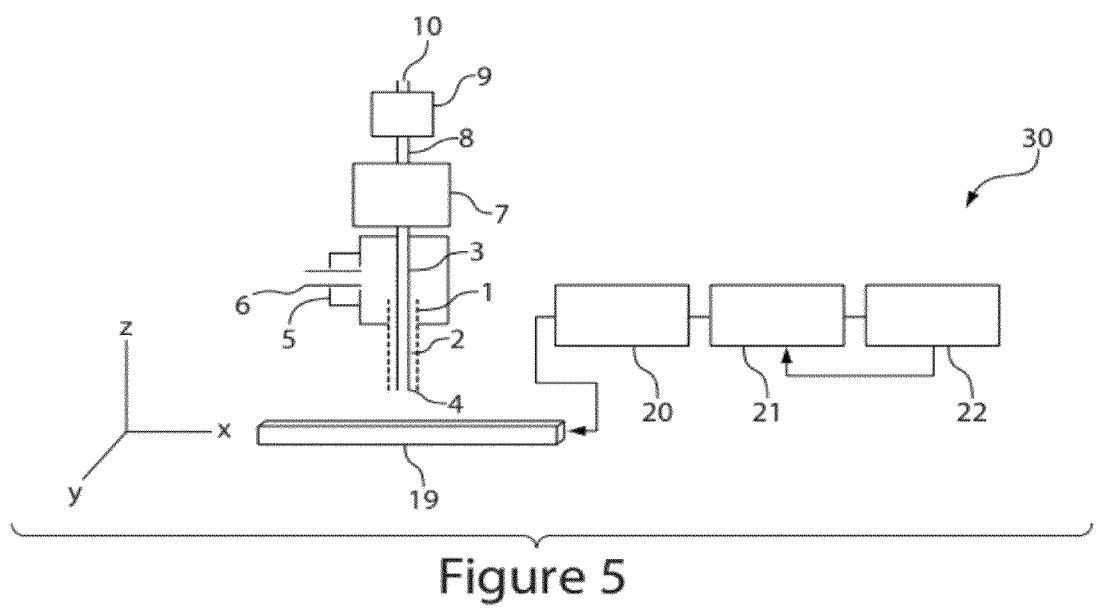
FIG. 5 shows a system wherein the hand piece is mounted on a robotic platform and is automatically positioned with respect to the sample surface having motion in three dimensions, X, Y, Z, and rotation between the XY, XZ, or YZ axis.

FIG. 5 shows a robotic embodiment of the system 100, wherein the target sample surface is located on a robotic platform 19. The platform 19 is coupled to a robotic movement system 30, including a motor 20, a motion controller 21, and computer 22 and may have other suitable position sensors (not shown) or controls known in the robotic art. The system is configurable such that platform 19 is moveable in three dimensions, i.e. x, y and z, and can be controlled remotely via the robotic system 30 to automatically sample and compile analysis data associated with the designated sampling points on the target surface.

Figure 6:
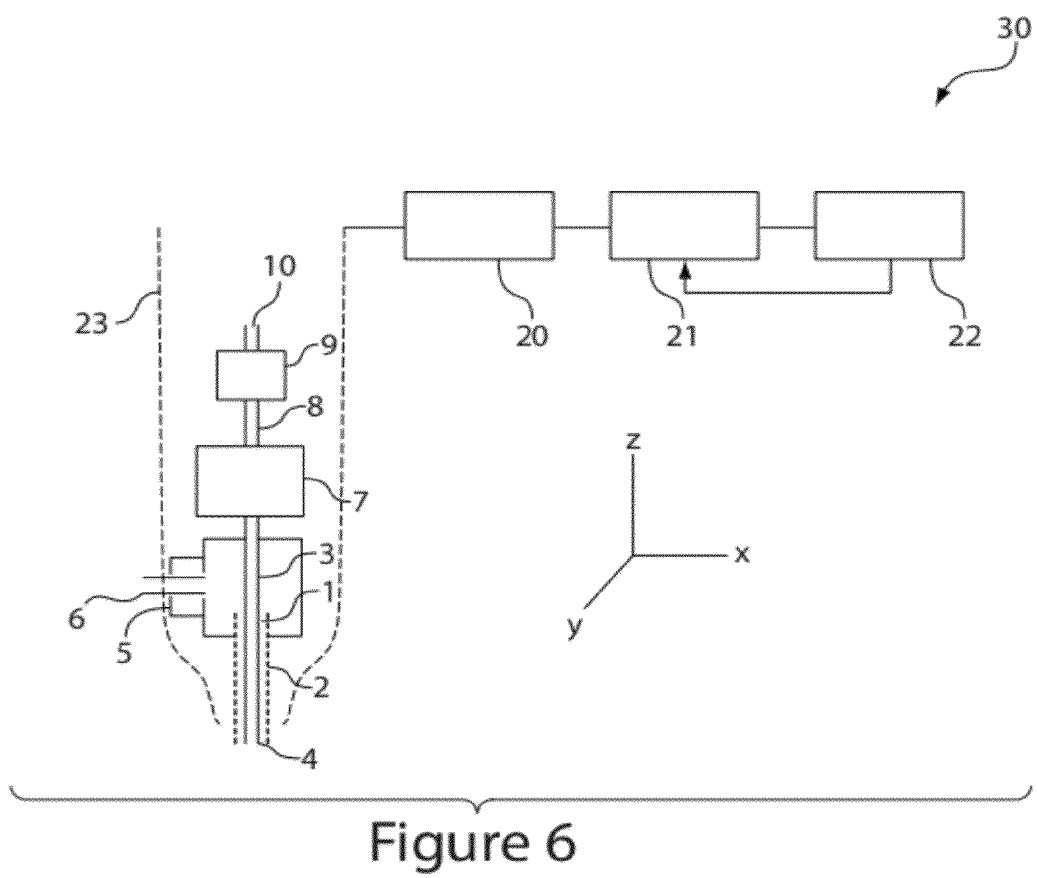
FIG. 6 shows a system wherein the hand piece is stationary and positioned orthogonal to the plane of a robotic platform having motion in three dimensions, X, Y, and Z on which the sample is placed for analysis.

FIG. 6 shows an embodiment of a system 100 embodied in a hand-piece mounted in a casing or housing 23. The hand-piece having a casing or housing 23 is coupled to a robotic movement system 30 capable of movement in three dimensions, i.e. x, y, and z, and rotatable about independent axes via remote control of the robotic system 30 so as to be positionable for probing points on the surface of a target object. The robotic system may be integrated with other sensing and control elements, and with out put data from the analysis instrument, to provide a graphic or pictorial representation of the probed object and the analysis results obtained from sample points on the object surface.

Several examples will illustrate benefits and operation of sampling probes for different purposes.

EXAMPLE 1

Figure 7:
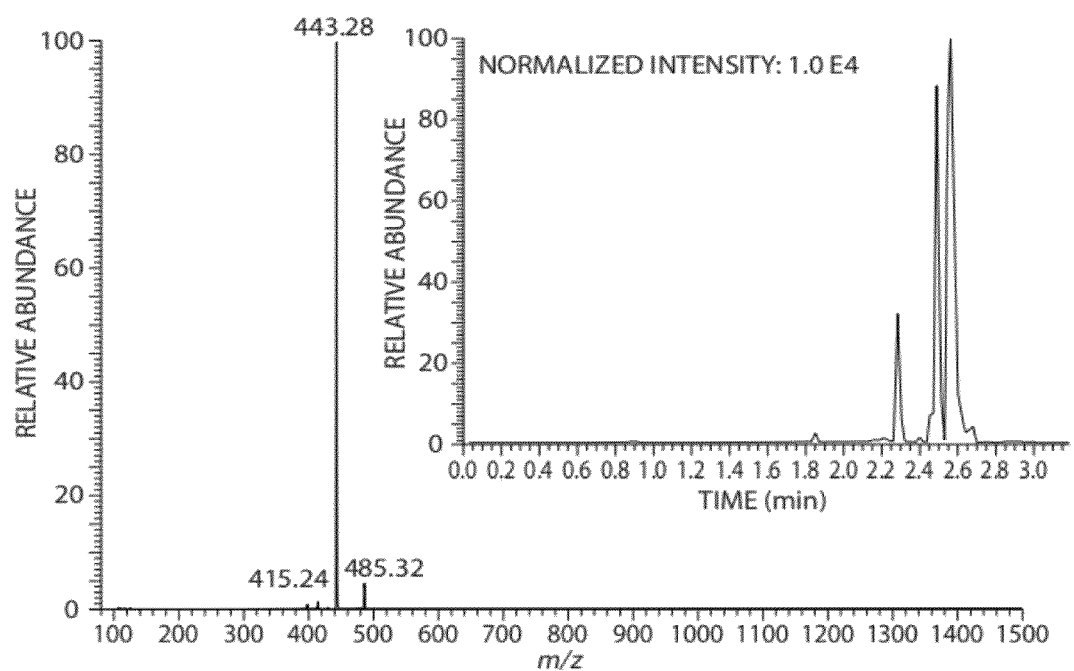
FIG. 7 shows detection spectrum of a heavy dye sampled from a polymer surface.

Rhodamine dye (molecular weight 443) was deposited on an inert Teflon surface and was sampled by the probe head using an irrigant/solvent desorption solvent comprised of a 50:49.9:1 mixture of acetonitrile, water and formic acid, using a 40 kHz drive signal at 50 W power. The aspirated flow was coupled as the input to a Thermo Scientific LTQ linear ion trap mass spectrometer. FIG. 7 shows the selected ion current at m/z 443 and the normalized intensities.

EXAMPLE 2

Figure 8:
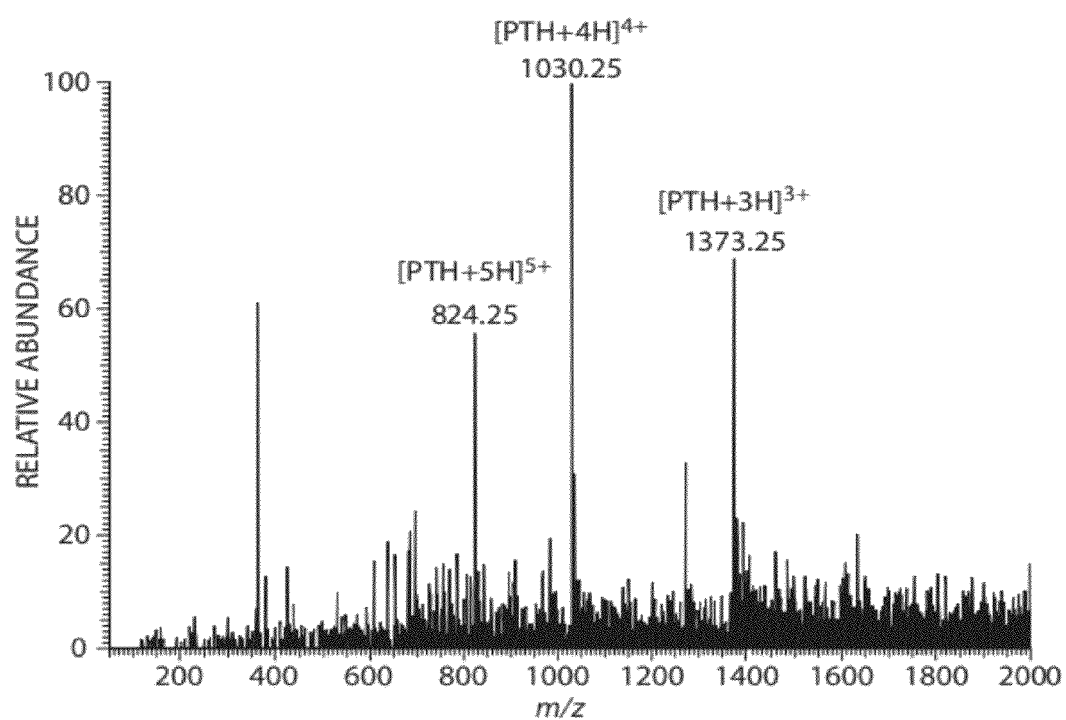
FIG. 8 shows a complex spectrum of parathyroid hormone sampled from a titanium surface.

Parathyroid hormone (PTH), of molecular weight (MW) 4117 was deposited onto a titanium surface and was then sampled and analyzed as in Example 1. The protonated ions were detected as shown in the spectrum of FIG. 8.

EXAMPLE 3

Figure 9:
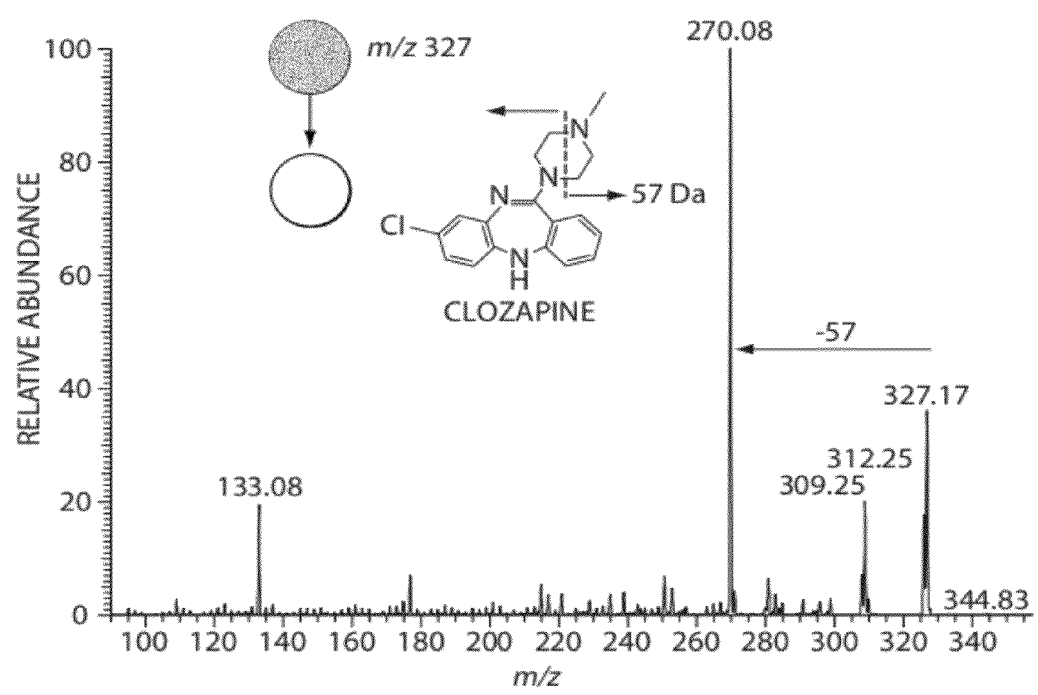
FIG. 9 shows the mass spectrum of a drug sampled from an intact rat kidney.

After dosing with clozapine at 50 mg/kg, a rat was sacrificed and the probe was used to gather a sample from an intact kidney. FIG. 9 shows the MS/MS mass spectrum of m/z 327±1.5 corresponding to the protonated ion of clozapine (MW: 326), sampled as in Examples 1 and 2. The inset shows the structure and the site of cleavage of the ion resulting in a neutral loss of 57 Daltons and the resultant ion at m/z 270.

EXAMPLE 4

Figure 10:
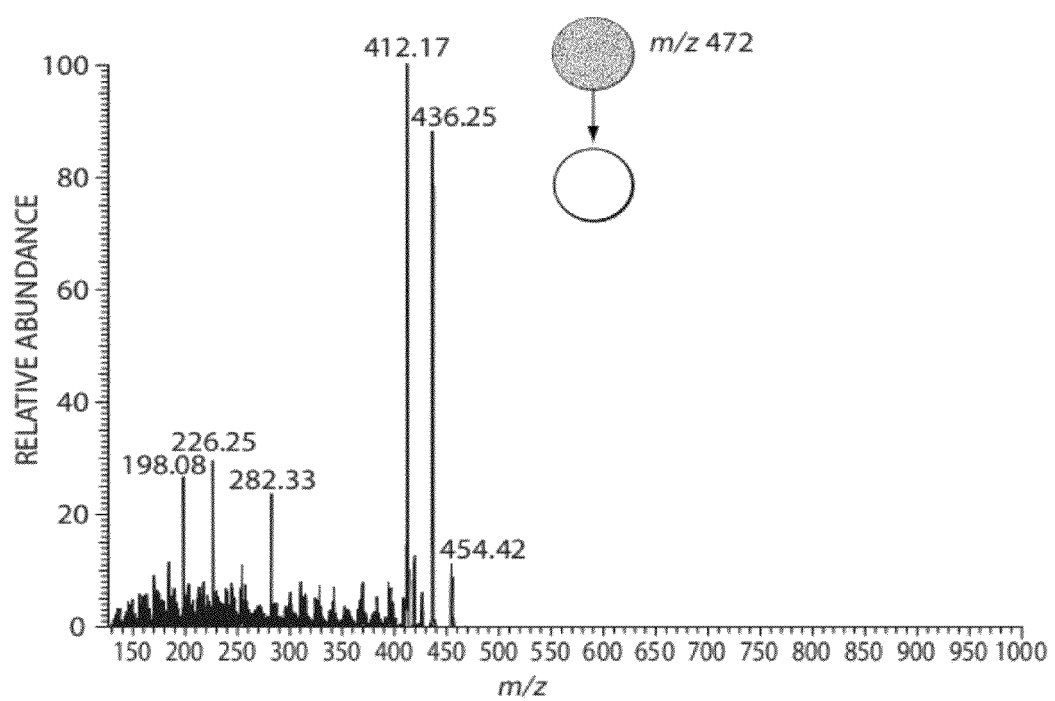
FIG. 10 shows the mass spectrum of a protonated sample of another drug sampled by the probe from a dried blood spot on a filter paper.

The MS/MS mass spectrum of m/z 472±1.5 corresponding to the protonated ion of terfenadine (MW: 471) as shown in FIG. 10 was taken of a sample desorbed from a dried blood spot on a Whatman 31 ETF filter paper, using the ultrasonic probe operated at 40 kHz, 50 W coupled to the Thermo Scientific LTQ linear ion trap mass spectrometer. Terfenadine concentration is 10 µg/mL; collision energy 22 arb units; with a desorption solvent system 80:19.9:0.1 of acetonitrile:water:formic acid.

Thus, the invention provides a novel probe adapted to effectively sample analytes present in and desorbed from an almost arbitrary range of target surfaces under ambient conditions, and to provide the sampled analyte as an effectively analyzable effluent stream to an analysis instrument, either directly, or after further steps of ionization, partial cleavage or reaction, aspiration, nebulization or desolvation. The invention being thus disclosed and illustrative embodiments thereof described and illustrated, further variations will occur to those skilled in the art and are considered to be within the scope of the invention, as described herein and in the claims appended hereto.

What is claimed is:

1. A system for desorption and sampling of analyte present on a target surface the system comprising:

a sonication probe including a capillary having a probe inlet end and a probe outflow end, the probe inlet end comprising a sampling tip and the probe outflow end being in fluid communication with the probe inlet end, the probe being coupled to a transducer so as to apply vibrational energy to the target surface at the probe inlet end for desorbing analyte from the surface;

an irrigation assembly having an irrigation outlet end positioned proximate to or coaxially with the sonication probe sampling tip for providing a flow of irrigation fluid proximate to the probe inlet end, and at least one aspirator located and connected to aspirate a sample of desorbed analyte and irrigation fluid into the capillary probe inlet end from the target surface for passage through the capillary to an analysis instrument.

2. The system according to claim 1, further characterized by at least one of the following: the analysis instrument has an atmospheric inlet located adjacent to the aspirator; the sonication probe comprises two sonication capillaries located coaxially to one another; a carrier gas conduit is positioned proximate to or coaxially with the sonication probe and/or the irrigation outlet, and operable to provide a flow of carrier gas to enhance transport of desorbed analyte into the capillary probe inlet; the carrier gas conduit further comprises a connector having a port for entry of carrier gas; the carrier gas is selected from a group comprising nitrogen, argon, helium, and air; an ionization assembly is located between the sampling tip and an atmospheric inlet of an analysis instrument; the analysis instrument is an instrument for analyzing ionized analyte and is selected from a group consisting of a spray ionization type instrument, a chemical ionization, a glow ionization or a laser ionization type instrument; the ionization assembly is located in a chamber; the ionization assembly is coupled to the sonication probe via a conduit; the at least one aspirator comprises a second aspirator located between the ionization assembly and the analysis instrument; the irrigation inlet end of the irrigation capillary further comprises a connector having a port for entry of irrigation fluid; the sonication probe, the irrigation capillary and the transducer are mounted within a hand-piece having a casing; the hand-piece having a casing is mounted on a robotic platform; the sample surface is mounted on the robotic platform; the at least one aspirator is attached to the hand-piece having a casing; the instrument is selected from a group of mass spectrometers consisting of time-of-flight, quadrupole, and triple quadrupole mass spectrometers or is an ion mobility spectrometer.

3. The system according to claim 2, wherein either the chamber or the conduit is heated.

4. The system according to claim 1, wherein the irrigation fluid is characterized by at least one of the following: substantially aqueous; and, a temperature that is adjustable, wherein the fluid is at least cooler than room temperature or is at least as warm as room temperature.

5. The system according to claim 1, wherein the sonication probe comprises a metal or a conductive polymer, the metal or polymer having a low acoustic impedance.

6. The system according to claim 1, wherein the sonication probe is adapted and configured with an ultrasonic cutting, ablation or cautery surgical tool that applies vibrational energy to a tissue target surface with an active tip, and wherein the capillary inlet and irrigation assembly are positioned proximate to the active tip to aspirate analyte from the tissue contacted by the tip.

7. A method for desorbing an analyte on a sample surface for molecular analysis, the method comprising:
   irrigating the analyte on the sample surface with an irrigation fluid in a system having at least one sonication probe at a selected distance and orientation in relation to the sample surface, wherein the at least one sonication probe comprises a capillary having a probe inlet end and a probe outflow end, the probe inlet end comprising a sampling tip and the probe outflow end, the capillary being coupled to an ultrasonic transducer for applying ultrasonic energy to the sample surface to vibrationally enhance desorption or release of analyte from the surface; and
   aspirating the released analyte into the sampling tip, through the capillary, and into a sample inlet of an instrument for analyzing composition of sample molecules, thereby effectively providing analyzable samples of analyte released from the surface for molecular analysis.

8. The method according to claim 7, wherein the at least one sonication probe comprises two sonication probes located coaxial to one another.

9. The method according to claim 7, further comprising at least one of the steps of: directing a flow of carrier gas at the analyte on the sample surface, and ionizing the aspirated analyte in an ionization source.

10. The method according to claim 9, wherein the carrier gas is selected from a group comprising nitrogen, argon, helium, and air.

11. The method according to claim 9, wherein the ionization source is selected from a group consisting of electrospray ionization (ESI), sonic spray ionization (SSI), atmospheric pressure chemical ionization (APCI), direct analysis in real time (DART), flowing afterglow of an atmospheric pressure glow discharge, and matrix assisted laser desorption ionization (MALDI).

12. The method according to claim 9, wherein the ionization source is further characterized by at least one of: being located in a chamber, and attached to the sonication probe via a conduit.

13. The method according to claim 12, further comprising the step of heating at least one of the chamber or the conduit.

14. The method according to claim 7, further comprising the step of dissolving molecules of the analyte in the irrigation fluid, prior to the step of aspirating molecules of the analyte into the sampling tip, through the capillary, and into the instrument.

15. The method according to claim 7, wherein the irrigation fluid is substantially aqueous.

16. The method according to claim 7, further comprising the step of adjusting the temperature of the irrigation fluid to be at least cooler than room temperature or at least as warm as room temperature.

17. The method according to claim 7, wherein the instrument is selected from a group of tandem mass spectrometers consisting of time-of-flight, Fourier transform ion cyclotron mass spectrometer, Orbitrap mass spectrometer, quadrupole, and triple quadrupole mass spectrometers or wherein the instrument is an ion mobility spectrometer.

18. The method according to claim 7, wherein the at least one sonication probe comprises a metal having low acoustic impedance or a conductive polymer having low acoustic impedance.

19. A method for constructing a device for desorption of an analyte from a target sample surface under ambient conditions for molecular analysis, the method comprising the steps of:
   coupling an ultrasonic transducer to a probe comprising a capillary having an inlet end and a distal end, wherein the ultrasonic transducer produces vibrations in the capillary,
   positioning an irrigation source to irrigate a target surface located proximate to the inlet end of the capillary, and
   providing at least one aspirator between a sampling tip and an inlet of an instrument for analyzing sampled analyte,
   wherein by positioning the probe at the target surface, analyte is effectively desorbed from the surface and picked up by the probe and provided to the instrument for analysis.

20. The method according to claim 19, wherein the instrument is further characterized in that it is at least one of: attached adjacent to the aspirator, and wherein the at least one probe comprises two sonication probe elements located coaxially to one another; and wherein the method further comprises the step of attaching a carrier gas capillary coaxial to the probe and an irrigation capillary, the carrier gas capillary having a carrier gas inlet end and a carrier gas outflow end.

21. The method according to claim 20, further comprising at least one of the steps of: attaching the carrier gas inlet end to a source of carrier gas for a gas flow; and attaching the inlet end of the carrier gas capillary to a connector having a port for entry of carrier gas; and wherein the carrier gas is selected from a group comprising nitrogen, argon, helium, and air.

22. The method according to claim 19, further comprising the step of attaching an ionization source between the sampling tip and the instrument.

23. The method according to claim 22, wherein the ionization source is selected from a group consisting of electrospray ionization (ESI), sonic spray ionization (SSI), atmospheric pressure chemical ionization (APCI), direct analysis in real time (DART), flowing afterglow of an atmospheric pressure glow discharge, and matrix assisted laser desorption ionization (MALDI).

24. The method according to claim 22, further comprising at least one of the following steps: enclosing the ionization source in a chamber; and attaching the ionization source to the sonication probe via a conduit.

25. The method according to claim 19, wherein the at least one aspirator comprises a second aspirator.

26. The method according to claim 25, further comprising the step of attaching the second aspirator between the ionization source and the instrument.

27. The method according to claim 19, further comprising at least one of the following steps: attaching an inlet end of an irrigation capillary to a connector having a port for entry of irrigation fluid; mounting a sonication probe, the irrigation capillary and the transducer within a hand-piece having a casing; mounting the hand-piece having a casing on a robotic platform; mounting the sample surface on a robotic platform; and, attaching the at least one aspirator to the hand-piece having a casing.

28. The method according to claim 27, wherein the sonication probe comprises a metal having low acoustic impedance or a conductive polymer having low acoustic impedance.

29. The method according to claim 27, wherein the irrigation fluid is substantially aqueous.

30. The method according to claim 19, wherein the instrument is selected from a group of tandem mass spectrometers consisting of time-of-flight, quadrupole, and triple quadrupole mass spectrometers; or wherein the instrument is an ion mobility spectrometer.

* * * * *